US00PP32015P2

(12) United States Plant Patent
Bradford et al.

(10) Patent No.: US PP32,015 P2
(45) Date of Patent: Jul. 28, 2020

(54) PLUM TREE NAMED 'PLUMCANDY XVI'

(50) Latin Name: *Prunus salicina*
Varietal Denomination: Plumcandy XVI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/501,444

(22) Filed: Apr. 17, 2019

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472; A01H 5/08
See application file for complete search history.

(56) References Cited

U.S. PATENT DOCUMENTS

PP14,220 P2 10/2003 Bradford
PP19,527 P2 12/2008 Bradford

*Primary Examiner* — Keith O. Robinson

(57) ABSTRACT

The present invention relates to a plum tree and more particularly to a new and distinct variety broadly characterized by a large size, vigorous, hardy, and productive tree. Being self-unfruitful, the present variety requires cross pollination from another plum or interspecific tree that blooms during the mid to late season, such as 'September YUMMY®' plum tree (U.S. Plant Pat. No. 14,220). The present variety's moderate blossom density and abundant pollen production entices strong bee activity to facilitate pollination. The fruit matures under the ecological conditions described during mid to late September, with first picking on Sep. 20, 2018. The fruit is uniform, large in size, very dark red in skin color, clingstone in type, mostly yellow in flesh color, firm in texture, juicy, and outstanding in flavor.

1 Drawing Sheet

Botanical classification: *Prunus salicina.*
Variety denomination: 'PLUMCANDY XVI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of plum tree, which has been denominated varietally as 'Plumcandy XVI'.

During a typical blooming season we isolate as seed parents both individual and groups of different plum and interspecific trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'Black Majesty' plum tree (U.S. Plant Pat. No. 19,527) was crossed by us in this manner. To pollinate this plum tree, we selected bouquets from several sources of plum trees without keeping specific written details. Upon reaching maturity the fruit from this plum tree was harvested, and the seeds were removed, cracked, stratified and germinated as a group with the label "H21". They were grown as seedlings on their own root in our greenhouse and upon reaching dormancy transplanted to a cultivated area of our experimental orchard located near Le Grand, Calif. in Merced County (San Joaquin Valley). During the summer of 2012 the claimed variety was selected by us as a single plant from the group of seedlings described above. Subsequent to origination of the present variety of plum tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Black Majesty' (U.S. Plant Pat. No. 19,527) plum tree, by being a medium to large tree, by being vigorous, by blooming in the mid to late season, by being self-unfruitful, by being productive and by producing fruit that is mostly globose in shape, mostly orange yellow in flesh color, very sweet, juicy, and firm, but is distinguished therefrom by producing fruit that is very dark red instead of black in skin color, that is much larger in size, and that ripens about ten days later.

The present variety is most similar to 'September YUMMY®' (U.S. Plant Pat. No. 14,220) plum tree by having a large and vigorous tree, by being self-unfruitful, by blooming in the mid to late season, by being productive, and by producing fruit that is fairly globose in shape, that is firm in texture, that is mostly red in skin color, that is mostly yellow in flesh color, and that matures in mid to late September, but is distinguished therefrom by producing fruit that is much sweeter in flavor, that is clingstone instead of semi-freestone in type, and that is larger in size.

The present variety is compared and referenced several times in this application to 'September YUMMY®' (U.S. Plant Pat. No. 14,220), including the abstract and claim. It is to be noted that "YUMMY®" is a United States Trademark, Ser. No. 75/618,722, owned by Johnny Appleseed Holdings Limited, Saint Georges Road South RD2, Hastings, New Zealand. Permission to use has been granted to the applicant by contract.

SUMMARY OF VARIETY

The present plum variety is characterized by a large size, vigorous, hardy, and productive tree. Being self-unfruitful, the present variety requires cross pollination from another plum or interspecific tree that blooms during the mid to late season, such as 'September YUMMY®' plum tree (U.S. Plant Pat. No. 14,220). The present variety's moderate blossom density and abundant pollen production entices strong bee activity to facilitate pollination. The fruit matures under the ecological conditions described during mid to late September, with first picking on Sep. 20, 2018. The fruit is uniform, large in size, very dark red in skin color, clingstone in type, mostly yellow in flesh color, firm in texture, juicy, and outstanding in flavor.

DRAWING

The accompanying photograph exhibits four whole fruits positioned to display the characteristics of the skin color and form, one divided fruit to reveal the flesh and stone, typical leaves, and two insets depicting the flower buds and blossoms as they appeared on the tree during the blooming season.

POMOLOGICAL CHARACTERISTICS

Referring now more specifically to the pomological characteristics of this new and distinct variety of plum tree, the following has been observed under the ecological conditions prevailing near Le Grand, Merced County (San Joaquin Valley), Calif., and was developed at the state of firm ripe on Sep. 25, 2018, on the original tree during its eleventh growing season. All major color code designations are by reference to the Inter-Society Color Council, National Bureau of Standards. Common color names are also used occasionally.

PARENTAGE

Seed parent: 'Black Majesty' (U.S. Plant Pat. No. 19,527) plum tree.
Pollen parent: Unknown.

TREE

Size: Large, reaching and maintaining a height of 12' [3.66 m.] and a spread of 10' [3.05 m.] after eleven growing seasons utilizing typical dormant pruning.
Vigor: Vigorous, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase formed type.
Hardiness: Hardy with respect to central California winters.
Heat tolerance: Observed to perform adequately in typical central California climatic conditions, which typically include prolonged periods of heat.
Drought tolerance: Variety is developed for commercial orchards and requires regular irrigation.
Production: Productive, thinning usually necessary.
Fertility: Self-unfruitful, requiring cross pollination by a suitable mid seasonal blooming plum or interspecific, such as 'September YUMMY®' plum tree (U.S. Plant Pat. No. 14,220).
Bearing: Regular bearer, weather dependent, no crop failures observed as of yet.
Leaf bud burst: Late, toward the end of flowering.
Trunk:
- *Size*.—Stocky, medium, reaching a maximum diameter of 3½" [88.9 mm.] after eleven growing seasons.
- *Texture*.—Medium roughness, shaggy.
- *Bark color*.—A Grayish brown [61. gy.Br] and Moderate brown [58. m.Br] variegation with Deep brown [56. deep Br] crevices present.
- *Lenticels*.—Approximate Number Per Square Inch: 6. Color: Grayish brown [61. gy.Br]. Typical Size: ¼" [6.4 mm.] in length. The width is typically one fourth as much as the length. Shape: Eye-shaped.

Branches:
- *Size*.—Diameter of the scaffold is 2¼" [57.2 mm.] measured 12" above the crotch, diameter of limb is 1¼" [31.8 mm.] measured 12" above the first fork.
- *Texture*.—Medium, shaggy on first year wood, increasing roughness with age.
- *Color*.—1st Year Wood Topside: Grayish red [19. gy.R]. 1st Year Wood Underside: Brilliant yellow green [116. brill.YG]. 2nd Year Wood: A Deep brown [56. deep Br] and Dark brown [59. d.Br] variegation.
- *Lenticels*.—Number Per Square Inch: About 12 on second year wood. Color: Light yellowish brown [76. l.yBr]. Typical size: Small, 1/32" [0.8 mm.] in length. The width is typically one fourth as much as the length. Shape: Eye-shaped.

Leaves:
- *Size*.—Medium. Average Length: 4½" [114.3 mm.]. Average Width: 2" [50.8 mm.].
- *Arrangement*.—Alternate.
- *Thickness*.—Medium.
- *Form*.—Elliptical.
- *Apex*.—Acuminate.
- *Base*.—Acute with an average base angle of seventy-five degrees.
- *Surface*.—Smooth on both sides.
- *Color*.—Dorsal Surface: Moderate olive green [125. m.OlG]. Ventral Surface: Moderate yellow green [120. m.YG].
- *Red midvein*.—Absent.
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Light greenish yellow [101. l.gY].
- *Stipules*.—Number: 2 per leaf, up to 6 per growing tip. Average Length: ¼" [6.4 mm.]. Color: Light greenish yellow [101. l.gY] becoming Grayish red [19. gy.R] with age.
- *Glands*.—Number: 1 to 2. Position: Alternate, positioned at the intersection of the petiole and base blade. Form: Globose. Size: Small, 1/64" [0.4 mm.] in diameter. Color: Moderate greenish yellow [102. m.gY] becoming a Deep reddish brown [41. deep rBr] in the center with age.
- *Leaf buds*.—Pointed.

Flower buds:

*Hardiness*.—Hardy, with respect to central California blooming season.

*Diameter*.—Typically 3/16" [4.8 mm.] 1 week before bloom.

*Length*.—Typically 5/16" [7.9 mm.] 1 week before bloom.

*Form*.—Not appressed.

*Surface*.—Slightly pubescent.

*Color*.—White [263. White].

Flowers: Perfect, complete, usually a single pistil, about twenty stamens, five sepals and petal locations alternately positioned.

*Average flower diameter*.—1" [25.4 mm.].

*Average flower depth*.—5/16" [7.9 mm.] when fully open.

*Average pedicel length*.—3/8" [9.5 mm.].

*Number of petals*.—Five, no double blossoms observed.

*Petal arrangement*.—Overlapping.

*Petal shape*.—Oval to slightly obovate.

*Petal margin*.—Entire, somewhat wavy.

*Average petal diameter*.—7/16" [11.1 mm.].

*Average petal length*.—1/2" [12.7 mm.].

*Petal apex*.—Rounded.

*Petal base*.—Rounded to slightly cuneate.

*Petal color*.—White [263. White] on both sides.

*Anther color*.—Brilliant yellow [83. brill.Y].

*Pollen production*.—Abundant, bee enticing.

*Pollen color*.—Brilliant yellow [83. brill.Y].

*Stigma color*.—Pale greenish yellow [104. p.gY].

*Stigma position*.—Stigma is located about 1/8" [3.2 mm.] below the average anther position.

*Ovary*.—Non-pubescent.

*Sepal color*.—Brilliant yellow green [116. brill.YG] on both sides.

*Sepal length*.—5/32" [4.0 mm.].

*Sepal width*.—1/8" [3.2 mm.].

*Sepal shape*.—Ovate.

*Sepal apex*.—Elliptical to match the width and length.

*Average pistil length*.—1/2" [12.7 mm.].

*Average stamen length*.—5/16" [7.9 mm.].

*Stamen position*.—Typically located about 1/32" [0.8 mm.] below the petals.

*Ovary*.—Smooth.

*Fragrance*.—Moderate in degree with a slight hint of vanilla.

*Blooming period*.—Medium to late compared with other varieties, about the same day as 'Blackred XII' interspecific tree (U.S. Plant Pat. No. 20,892).

*Onset of bloom*.—One percent on Feb. 27, 2018.

*Date of full bloom*.—Mar. 12, 2018.

*Duration of bloom*.—One to two weeks, dependent on ambient temperature.

*Bloom density*.—Moderate.

*Number per cluster*.—Typically 2 or 3, up to 10 observed.

FRUIT

Maturity when described: Firm ripe, Sep. 25, 2018.

Date of first picking: Sep. 20, 2018.

Date of last picking: Oct. 15, 2018.

Size: Uniform, large.

*Average diameter axially*.—2 3/4" [69.9 mm.].

*Average diameter across suture plane*.—2 5/8" [66.7 mm.].

*Average diameter across cheek plain*.—2 5/8" [66.7 mm.].

*Typical weight*.—7.5 ounces [213 grams].

Form: Mostly uniform, symmetrical, globose to slightly elongated.

*Axial view*.—Round.

*Longitudinal section form*.—Round.

Suture: A distinct shallow trough extending from the base to the apex.

Suture depth: Shallow at the apex and along the side, medium toward the shoulder.

Ventral surface: Rounded.

Lips: Fairly equal.

Cavity: Flaring.

*Depth*.—1/2" [12.7 mm.].

*Breadth*.—7/8" [22.2 mm.].

*Stem markings*.—Occasional, Brilliant orange yellow [67. brill.OY] when present.

Base: Truncate, strongly cordate when viewed parallel to the suture.

Apex: Rounded.

Pistil point: An inconspicuous Pale orange yellow [73. p.OY] dot.

Stem: Medium size.

*Average length*.—11/16" [17.5 mm.].

*Average width*.—1/8" [3.2 mm.].

Skin:

*Thickness*.—Medium.

*Surface*.—Smooth.

*Tenacity*.—Tenacious to flesh.

*Astringency*.—Slight.

*Tendency to crack*.—None observed.

*Color*.—Very dark red [17. v.d.R] over a Dark red [16. d.R] background with moderate Strong orange yellow [68. s.OY] freckling throughout.

*Lenticels*.—Number Per Square Inch: About 100. Average diameter: 1/80" [0.3 mm].

*Bloom*.—Heavy.

Flesh:

*Color*.—Light orange yellow [70. l.OY] with Light yellow [86. l.Y] fibers throughout. Moderate red [15. m.R] streaking very near the skin occurs as the fruit matures.

*Surface of pit cavity*.—Covered with Brilliant yellow [83. brill.Y] broken fibers when twisted away from stone.

*Amygdalin*.—Moderate to abundant.

*Juice*.—Abundant, rich.

*Texture*.—Firm, crisp.

*Fibers*.—Abundant, fine, tender.

*Ripens*.—Fairly even.

*Flavor*.—A tasty blend of acid and sugar, typically 24 brix.

*Aroma*.—Very slight.

*Eating quality*.—Outstanding.

STONE

Type: Clingstone.

Form: Obovate.

Hilum: Narrow.

Base: Rounded to truncate.

Apex: Acute.
Sides: Fairly equal.
Surface: Rough throughout.
External color of stone: Dark orange yellow [72. d.OY].
Pit wall color when cracked: Light yellowish brown [76. l.yBr].
Cavity surface color: Strong yellowish brown [74. s.yBr].
Average pit wall thickness: ⅛" [3.2 mm.].
Average length: 1" [25.4 mm.].
Average width: ¾" [19.1 mm.].
Average breadth: ⅜" [9.5 mm.].
Tendency to split: None observed.
Kernel:

*Form*.—Oval.
*Pellicle color*.—Dark orange yellow [72. d.OY].
*Skin color*.—Dark orange yellow [72. d.OY].
*Vein color*.—Moderate yellowish brown [77. m.yBr].
*Taste*.—Bitter.
*Viable*.—Yes.
*Average length*.—9/16" [14.3 mm.].
*Average width*.—⅜" [9.5 mm.].

USE

Market: Fresh market and long distance shipping.
Keeping quality: Excellent. Fruit quality observed to remain in good condition after 30 days in standard cold room at 36° Fahrenheit [2° Celsius].
Shipping quality: Excellent.
Resistance to insects: Not tested.
Resistance to diseases: Not tested.

OTHER NOTES

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of plum tree, *prunus salicina*, substantially as illustrated and described, that is most similar to 'September YUMMY®' (U.S. Plant Pat. No. 14,220) plum tree by having a large and vigorous tree, by being self-unfruitful, by blooming in the mid to late season, by being productive, and by producing fruit that is fairly globose in shape, that is firm in texture, that is mostly red in skin color, that is mostly yellow in flesh color, and that matures in mid to late September, but is distinguished therefrom by producing fruit that is much sweeter in flavor, that is clingstone instead of semi-freestone in type, and that is larger in size.

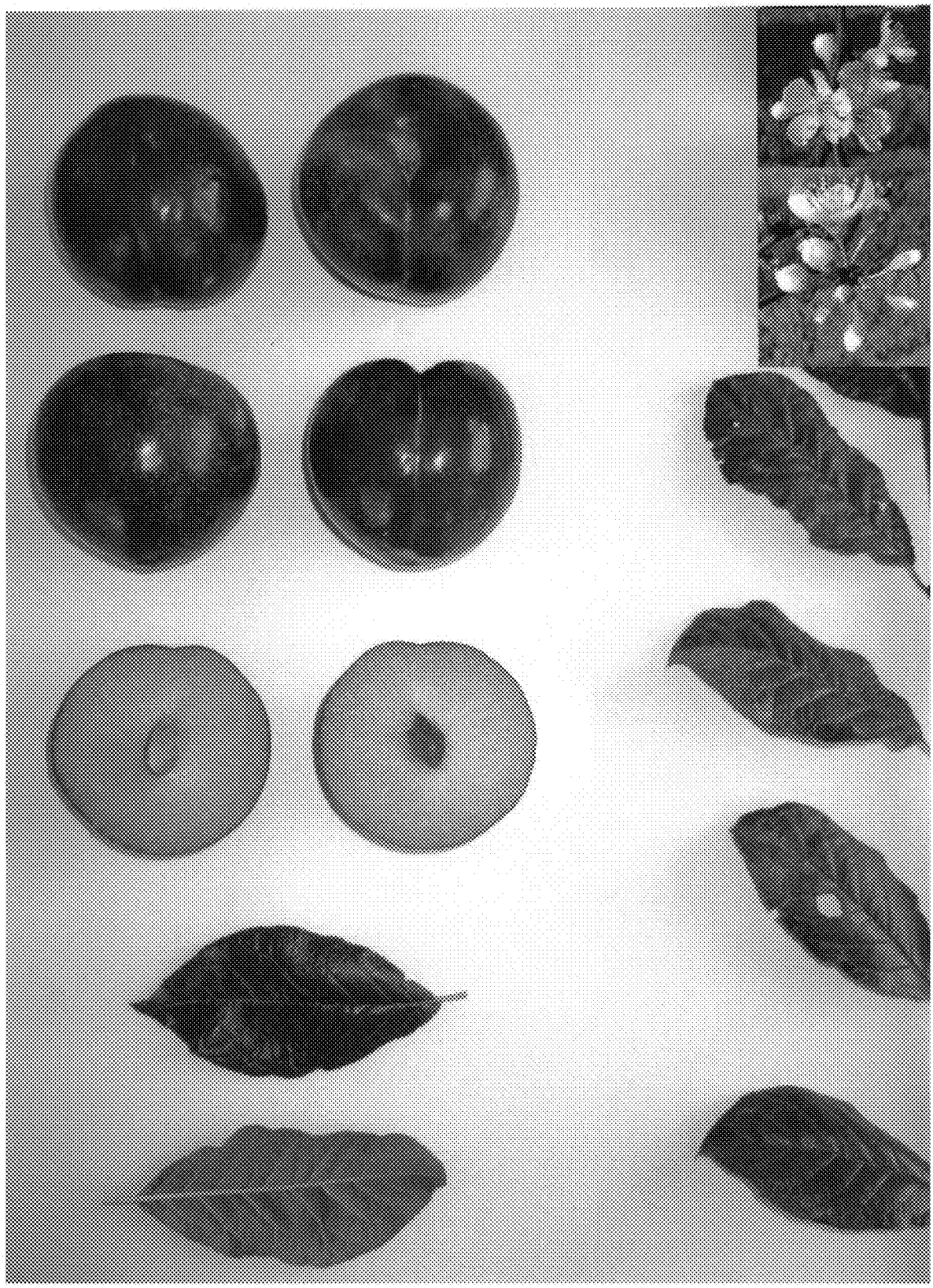

* * * * *